(12) United States Patent
Piccone

(10) Patent No.: US 8,475,421 B2
(45) Date of Patent: Jul. 2, 2013

(54) SHIELD ESPECIALLY ADAPTED FOR USE IN CONNECTION WITH CHANGING AN OSTOMY POUCHING SYSTEM

(76) Inventor: Jackie Lynn Piccone, Aurora, CO (US)

(*) Notice: Subject to any disclaimer, the term of this patent is extended or adjusted under 35 U.S.C. 154(b) by 419 days.

(21) Appl. No.: 12/819,259

(22) Filed: Jun. 21, 2010

(65) Prior Publication Data
US 2011/0313379 A1    Dec. 22, 2011

(51) Int. Cl.
*A61F 5/44* (2006.01)

(52) U.S. Cl.
USPC ........... 604/332; 604/337; 604/338; 604/343; 604/344

(58) Field of Classification Search
USPC .......................... 604/332, 337, 338, 343, 344
See application file for complete search history.

(56) References Cited

U.S. PATENT DOCUMENTS

| | | | |
|---|---|---|---|
| 5,248,308 | A | 9/1993 | von Emster |
| D369,662 | S | 5/1996 | Kuentz |
| 5,865,819 | A | 2/1999 | Cisko et al. |
| 6,740,067 | B2 * | 5/2004 | Leise et al. ............ 604/332 |
| 2009/0069764 | A1 | 3/2009 | Burlot et al. |
| 2009/0088712 | A1 | 4/2009 | Ryder et al. |

FOREIGN PATENT DOCUMENTS

| | | |
|---|---|---|
| FR | 2824472 | 11/2002 |
| GB | 2273052 | 6/1994 |

* cited by examiner

*Primary Examiner* — Jacqueline F. Stephens

(57) ABSTRACT

A shield that is useful in connection with an ostomy pouching system when changing a wafer or changing a collection pouch. The shield includes a plate adapted to be disposed over the stoma and at least a portion of the ostomy pouching system, an absorbent material adapted to absorb body waste flowing from the stoma, which absorbent material is disposed adjacent to a portion of the plate, and an adhesive or other mechanism for selectively securing the plate and the absorbent material proximate to the stoma such that the plate is disposed over the stoma when portions of the ostomy pouching system are changed. Also disclosed is the combination of an animal body and the shield, as well as a method of containing the flow of body waste from a stoma.

27 Claims, 2 Drawing Sheets

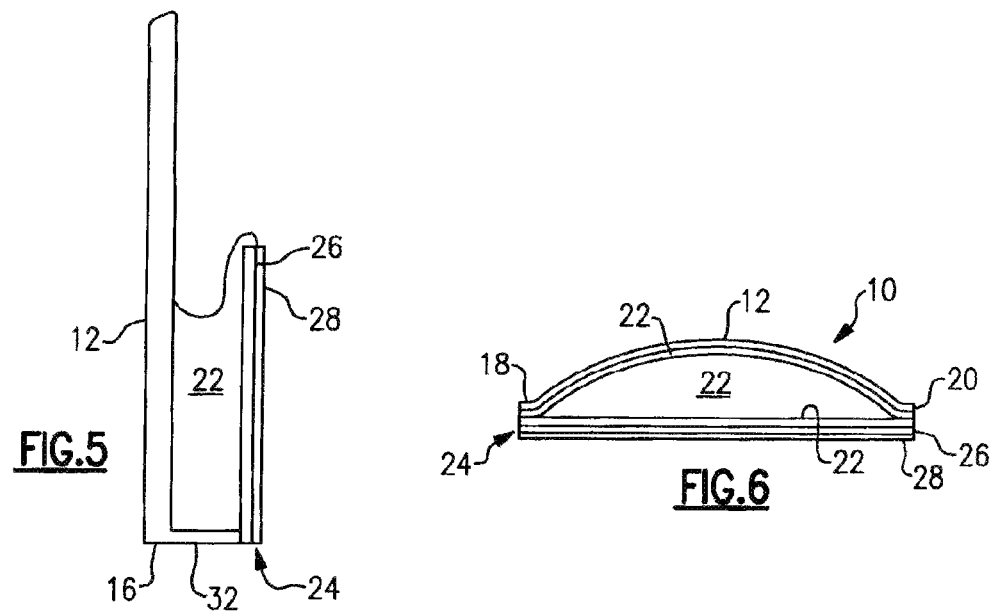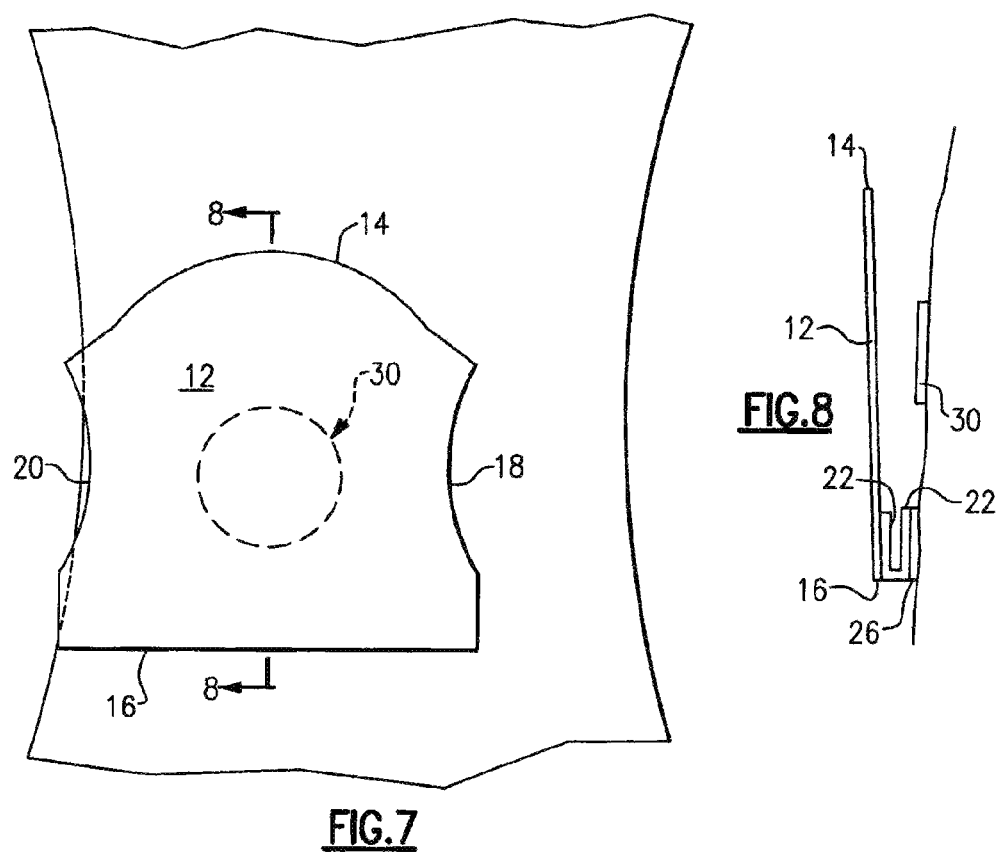

SHIELD ESPECIALLY ADAPTED FOR USE IN CONNECTION WITH CHANGING AN OSTOMY POUCHING SYSTEM

FIELD OF THE INVENTION

The present invention relates to a shield that is especially adapted to be used in connection with changing an ostomy pouching system and also to a method of using the shield.

BACKGROUND OF THE INVENTION

An ostomy pouching system is a medical prosthetic that provides a means for the collection of waste from a diverted biological system and is commonly associated with medical procedures such as colostomies, ileostomies, and urostomies. In such medical procedures, an internal body conduit, for example, an intestine, is surgically severed and connected to a hole in the skin of the body, such that the interior of the intestine is in communication with the environment exterior to the skin. The distal end of the conduit extending through the skin is commonly called a stoma. In general, a stoma is a surgically created opening that connects a portion of a body cavity to the outside environment. In a colostomy, for example, a surgically created opening in the large intestine allows the removal of feces out of the body, bypassing the rectum, to drain into a pouch or other collection device connected with the stoma.

In order to contain the waste flowing through a conduit such as an intestine and to a stoma, ostomy pouching systems have been designed to be selectively secured to the skin in the region around the stoma. Ostomy pouching systems usually consist of a mounting plate, commonly called a baseplate or a wafer, and a collection pouch that is attached mechanically or with an adhesive in a fluid-tight seal to the wafer. Wafers are manufactured in a variety of shapes, usually being fashioned of pectin or a similar organic material, which is adhered with a light adhesive so as to be selectively secured to the skin surrounding the stoma. An internal opening, usually centrally disposed, in the wafer is selectively sized so as to accommodate the stoma. The wafer protects the surrounding skin from contact with the waste flowing through the stoma.

Ostomy collection pouches generally comprise two basic types: an open-end, which is drainable, and a close-end, which is disposable. With close-end pouch collection systems, disconnecting a pouch from the associated wafer and reattaching a new pouch can be an extremely messy, foul procedure. Sometimes the pressure within the stoma or a back-up of body waste within the stoma can result in waste spurting out from the stoma. Even in those situations where body waste does not spurt from the stoma, usually there is an oozing of waste from the stoma.

In both open-end and close-end collection pouches, the wafer may last between four to ten days before it needs to be replaced, which time duration is highly dependent on the individual's lifestyle, the type of ostomy, and the person's anatomy. The same problems associated with spurting and oozing waste are attendant the act of changing a wafer. Situations also arise where the wafer peels away from the skin or where the connection between the wafer and the collection pouch becomes imperfectly sealed, such that waste from the stoma leaks from the wafer region.

Whenever possible, most persons fit with an ostomy pouching system prefer to change a close-end collection pouch or the wafer while in a bathroom shower. Nevertheless, there may be several different types of situations where a preferred environment is not attainable, such as where a leak occurs while the person is at a restaurant, at a sporting event, or traveling, or such as where a person is bedridden. Thus, it can be appreciated that there are various degrees of inconvenience and urgency in attending to the replacement of a close-end collection pouch or to the replacement of a wafer.

The present invention was developed in order to facilitate a relatively sanitary and safe way to change a close-end collection pouch or the wafer so that waste such as acidic fecal residue minimizes contact with the region of the skin surrounding the stoma and so that body waste is prevented from spewing and spilling onto a person's clothing, onto bedding, and onto other objects in the vicinity of the stoma. The invention may be conveniently, readily, and discretely available and employed in many environments and situations.

SUMMARY OF THE INVENTION

The present invention relates to a shield that is useful in connection with an ostomy pouching system when changing a wafer or changing a collection pouch. The shield includes a plate adapted to be disposed over the stoma and at least a portion of the ostomy pouching system, an absorbent material adapted to absorb body waste flowing from the stoma, which absorbent material is disposed adjacent to a portion of the plate, and an adhesive or other mechanism for selectively securing the plate and the absorbent material proximate to the stoma such that the plate is disposed over the stoma when portions of the ostomy pouching system are changed. Also disclosed is the combination of an animal body and the shield, as well as a method of containing the flow of body waste from a stoma.

BRIEF DESCRIPTION OF THE DRAWINGS

The present invention will be described with reference to the accompanying drawings, wherein

FIG. 5 is a cross-sectional view of yet another embodiment of the shield shown in FIG. 1 taken along the line 2-2;

FIG. 6 is a schematic top view of a shield such as that shown in FIG. 1 in accordance with still another embodiment of the present invention;

FIG. 7 is a schematic illustration of a shield shown in FIG. 1 secured against the torso of a human body and disposed over a wafer through which a stoma is centrally disposed; and FIG. 8 is a schematic cross-sectional view of the shield and torso shown in FIG. 7 taken along the line 8-8.

DESCRIPTION OF A PREFERRED EMBODIMENT

Figure 1:
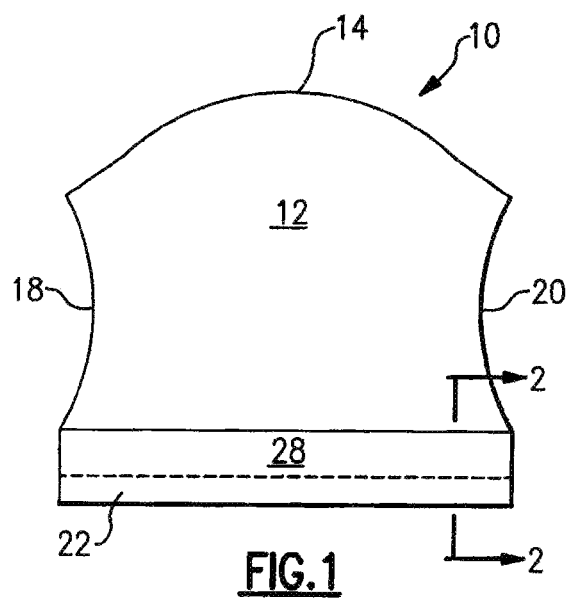
FIG. 1 is a plan view of a shield in accordance with one embodiment of the present invention.

The present invention will be described with reference to the accompanying drawings wherein like reference numerals refer to the same item.

The present invention relates to a shield that is especially useful in connection with an ostomy pouching system when changing a wafer or changing a collection pouch. There shown in FIG. 1 a shield 10 that includes a sheet or plate 12 of preferably clear plastic preferably having a relatively thin and uniform thickness. The top edge 14 of the plate 12 preferably possesses a convex periphery, and the lower edge 16 is preferably straight Each lateral edge 18, 20 of the sheet 12 is preferably arcurately indented.

Figure 2:
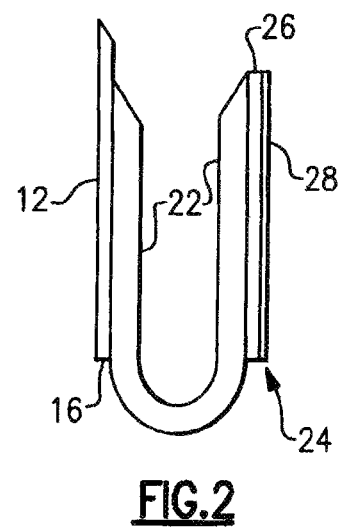
FIG. 2 is a cross-sectional view of the shield shown in FIG. 1 taken along the line 2-2.

Extending across the bottom of the plate 12 is an absorbent material 22 that may be fashioned as a layer of cotton, air-laid paper, superabsorbent polymers, or another absorbent material, such as materials used in surgical gowns and masks, used in feminine sanitary napkins and tampons, or used in diapers and in incontinence products. As shown in FIG. 2, which is a cross-sectional view taken along the line 2-2 in FIG. 1, the absorbent material 22 may be fashioned in the shape of a pocket or trough. The surface of the absorbent material 22 adjacent to the plate 12 may be secured to the plate such as by an adhesive or stitching.

A strip of adhesive 24 is disposed on the side of the absorbent material 22 opposite to the plate 12. The adhesive strip 24 may be composed of a dual layer comprising a preferably resilient or sponge-like base layer 26 coated with an adhesive and a peel-away layer 28. The base layer 26 may be secured to the absorbent material 22 by means such as an adhesive or stitching. The base layer 26 may also be formed of an absorbent material. The peel-away layer 28 is designed to be lightly adhered to the adhesive coating of the base layer 26 such that the peel-away layer 28 may be removed just prior to using the shield 10.

In use, the peel-away layer 28 is peeled away from the base layer 26, thereby exposing the light adhesive coating on the outer surface of the base layer 26. The shield 10 is then disposed adjacent to the torso of a person having an ostomy pouching system, as depicted in FIGS. 7 and 8. The dashed circular line 30 in FIG. 7 represents the outer peripheral contour of a wafer disposed adjacent to the person's skin and centered about the stoma (not shown). The base layer 26 is then pressed against the skin of the person immediately beneath the wafer 30, as best shown in FIG. 8. The base layer 26 will thereby be slightly adhered to the skin, and the plate 12 will be upstanding and slightly spaced from both the person's skin and the wafer 30. The adhesive coating on the outer surface of the base layer 26 is preferably strong enough so that the shield 10 is self-supportingly attached to the person's skin. Preferably the plate 12 will be substantially maintained in the range of about one to four inches away from the stoma, and more preferably about two to three inches away from the stoma. The plate 12 preferably may be deflected toward or farther away from the stoma by manual manipulation.

When the shield 10 is so disposed on a person's skin with the base layer 26 immediately beneath the wafer 30, the indented, lateral edges 18, 20 of the plate 12 facilitate a person's hands being interposed between the skin and the plate 12 so that the person's hands may manipulate the collection pouch (not shown) or the wafer 30. It will be appreciated that when the shield 10 is so secured to a person's skin, any spurting of waste through the stoma disposed centrally in the wafer 30 will be blocked by the interiorly facing surface of the plate 12 and will flow downwardly toward the absorbent layer 22. Also, any waste seeping from the stoma will likewise drain downwardly along the person's skin, however, the strip of base layer 26 preferably having a continuous adhesive coating applied against the person's skin blocks further flow of the waste downwardly along the person's skin and will direct the waste toward the absorbent layer 22. Where the absorbent material 22 is preferably fashioned as a pocket, any particulate material in the waste is collected within the pocket of the absorbent material 22. Any liquid waste will be absorbed by and maintained in the absorbent material 22.

The area in the region of the wafer 30 may be cleaned, powdered, or otherwise treated, and then either or both the collection pouch and the wafer 30 may be replaced. When the collection pouch and/or the wafer has been replaced, then the shield 10 may be removed from the person's skin by gently pulling on one end of the base layer 26. The shield 10 may then be discarded in the trash or another suitable disposal system.

It should be appreciated that the plate 12 is preferably formed of a relatively thin sheet of material that may be manually bendable into a substantially curved configuration about the torso of a person fitted with an ostomy pouching system, as shown in FIGS. 7 and 8. With such a construction, the portion of the plate 12 adjacent to the lower peripheral edge 16 may assume a curved configuration to adapt to the contour of the human torso, and the upper portion of the plate 12 will be likewise curved so as to better contain any waste squirted from the stoma. In practice, the base layer 26 is preferably adhesively applied to the skin beneath the stoma in a concave line, in a smile shape, which will tend to curve the plate 12 into a cupped shape. It is also within the contemplation of the present invention that the plate 12 may be preformed into a substantially curved or bowed configuration. In such a preformed construction, the portion of the plate 12 near the lower peripheral edge 16 may be only slightly curved and the upper portion of the plate 12 may possess a more pronounced curved or cupped configuration. The invention also contemplates that the adhesive strip 24 and the lower edge of the plate 12 may be concave, rather than straight, so as to help facilitate contaminant of the waste.

The plate 12 may be fashioned of a variety of different materials, but is preferably fashioned from plastic or paper, and preferably a clear plastic so that either the person fitted with the ostomy pouching system or a health care practitioner may see through the plate 12 and view the wafer and the collection pouch as well as the condition of the stoma, the skin surrounding the stoma and the wafer, and any waste being emitted from the stoma.

Preferably the plate 12 possesses a surface area facing the stoma substantially in the range of about twenty to one hundred forty square inches. And very preferably about fifty to eighty square inches. The surface area of the plate 12 is preferably larger for big people and is smaller for smaller people such as children. The invention contemplates that shields 10 may be manufactured with plates 12 having a selected variety of surface areas such as twenty square inches, fifty square inches, and one hundred twenty square inches. Such manufacturing will offer customers a few different sizes of shields 10 from which to select.

The plate 12 also is preferably non-collapsible so that when the shield 10 is selectively secured to the torso of a body, as depicted in FIGS. 7 and 8, the plate 12 will stand self-supportingly in a generally upright configuration over and slightly spaced from the wafer 30 and any associated collection pouch.

Although FIGS. 7 and 8 depict the shield 12 as would be preferably secured to the torso of a person who is standing or sitting in an upright position, it should be appreciated that the shield 10 may be selectively secured to the body while reclined, prostrate, or in another position so that the absorbent material 22 is disposed vertically below the stoma such that any waste emitted from the stoma will flow downward, onto the absorbent material 22. It will also be appreciated by those persons who are fitted with ostomy pouching systems and by those who care for such persons that the shield 10 may be advantageously employed when such persons are about to leave a shower, while they dry off, and until they can install a new wafer or collection pouch.

Figure 3:
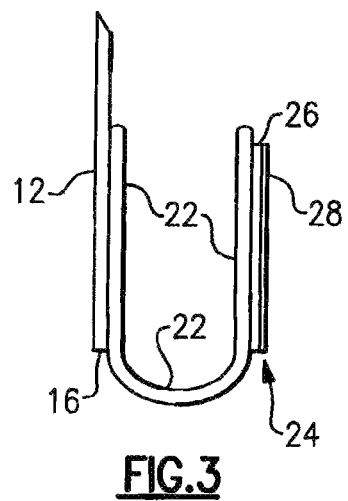
FIG. 3 is a cross-sectional view of another embodiment of the shield shown in FIG. 1 also taken along the line 2-2.
Figure 4:
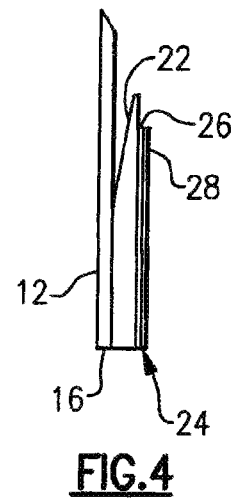
FIG. 4 is a cross-sectional view of a different embodiment of the shield shown in FIG. 1 taken along the line 2-2.

Other embodiments of the shield 10 are depicted in FIGS. 3-6. FIGS. 3-5 are cross-sectional views of different embodiments of the shield 10 taken along the line 2-2 in FIG. 1, whereas FIG. 6 is a top schematic view of another embodiment of the shield 10.

In the embodiment shown in FIG. 3, the absorbent material 22 is fashioned of a flexible material such that the lower portion of the absorbent material 22 sags or droops. The embodiment shown in FIG. 3 may be further modified by fabricating the absorbent material 22 so that it is relatively thicker in the lower region thereof, where the absorbent material 22 sags. Also, in the embodiment shown in FIG. 3, the lower surface of the absorbent material 22 in the region of the sag may be further coated with a fluid impermeable substance so that body waste emitted from the stoma does not seep through the absorbent material 22 and drip from the absorbent material 22. Such a coating may be fashioned of a plastic, a rubber, Teflon®, or other material.

In the embodiment depicted in FIG. 4, the upper edge of the absorbent material 22 is angled or beveled so as to direct waste toward the inner surface of the plate 12 and further down into the pocket region between the absorbent material 22 and the plate 12.

The embodiment of the shield 10 depicted in FIG. 5 includes a relatively thick absorbent material 22 between the shield 12 and the adhesive strip 24. The upper surface of the absorbent material 22 forms a concave depression so as to help direct waste to the middle of the absorbent material 22, where the waste can flow into and through the absorbent material 22 and can be dispersed within the absorbent material 22 in a more uniform manner so as to maximize the amount of waste that can be absorbed by the absorbent material 22. The lower peripheral edge 16 of the plate 12 shown in FIG. 5 possesses a lip or shelf 32 beneath the absorbent material 22 and extending to the adhesive strip 24. Such a shelf 32 is preferably fashioned of a fluid impermeable material so as to help prevent any waste from seeping through the absorbent material 22 and dripping from the bottom portion of the absorbent material.

In the embodiment depicted in FIG. 6, the plate 12 is preformed in a bowed, substantially arcuate configuration. The adhesive strip 24 extends straight across the plate 12, generally as an arcuate cord, and is secured to each lateral edge 18, 20 of the plate 12 by adhesive, stitching, or another means. Such construction helps maintain the plate 12 in a bowed configuration, which again, helps contain waste that squirts from the stoma. It can also be appreciated from viewing FIG. 6 that the thickness of the absorbent material 22 and the width of any pocket formed of the absorbent material 22 is widest and thickest toward the midway point between the lateral edges 18, 20 of the plate 12. Since the shield 10 will preferably centered over the stoma, the midway region between the lateral edges 18, 20 of the plate 12 will most likely be exposed to and have contact with a relatively greater amount of waste emitted from the stoma. Because the mouth of the pocket formed of the absorbent material 22 is widest at that midway region and the absorbent material 22 is most plentiful in that midway region, the waste can be more effectively captured and absorbed in that region.

While various embodiments of the present invention have been described herein, it will be appreciated that the invention includes embodiments other than those specifically illustrated or described and that changes in the form and arrangement of parts and the specific manner of practicing the invention may be varied without departing from the nature or scope of the invention. Consequently, the invention may be practiced otherwise than is specifically described above.

I claim:

1. A shield adapted for use in connection with changing portions of an ostomy pouching system in association with a stoma extending through the skin of a human torso and through which body waste flows, said shield comprising:
   a plate adapted to be disposed over and spaced away from the stoma, the torso skin immediately surrounding the stoma, and at least a portion of the ostomy pouching system;
   an absorbent material adapted to absorb body waste flowing from the stoma, said absorbent material disposed adjacent to a portion of said plate; and
   means for selectively securing said plate and said absorbent material proximate to the stoma such that said plate is disposed over and spaced away from the stoma, the torso skin immediately surrounding the stoma, and at least a portion of the ostomy pouching system and such that said absorbent material is disposed beneath the stoma and at least a portion of the ostomy pouching system.

2. The shield according to claim 1 wherein said securing means includes an adhesive.

3. The shield according to claim 1 wherein said securing means includes an adhesive layer covered by a sheet adapted to be peeled away from said adhesive layer in order to expose said adhesive layer such that said adhesive layer can be applied against the body proximate to the stoma.

4. The shield according to claim 1 wherein said plate is fashioned in a substantially planar configuration and is manually bendable into a substantially cupped configuration.

5. The shield according to claim 1 wherein said plate is preformed into a substantially cupped configuration.

6. The shield according to claim 5 wherein said cupped configuration comprises a substantially arcuate, bowed configuration.

7. The shield according to claim 1 wherein said plate is fashioned essentially of a material selected from the group consisting of plastic and paper.

8. The shield according to claim 1 wherein said absorbent material is fashioned in a pocket configuration.

9. The shield according to claim 1 wherein said absorbent material is maintained in a substantially abutting relation with a portion of said plate and wherein said securing means includes an adhesive layer maintained in a substantially abutting relation with said absorbent material.

10. The shield according to claim 1 wherein said absorbent material possesses a substantially pocket configuration extending along and maintained against the peripheral edge of said plate, with the mouth portion of the pocket facing away from the plate peripheral edge and wherein said securing means includes a strip of adhesive extending along and maintained against said absorbent material.

11. The shield according to claim 1 wherein a surface of said plate possesses an area substantially in the range of about twenty to one hundred forty square inches, which surface is adapted to face the stoma and at least a portion of the ostomy pouching system.

12. The shield according to claim 1 wherein said plate is adapted to be spaced in the range of about one to four inches away from the stoma and wherein said securing means secures said plate and said absorbent material proximate to the stoma such that said plate is spaced in the range of about one to four inches away from the stoma.

13. The shield according to claim 12 wherein said plate is adapted to be spaced in the range of about two to three inches away from the stoma and wherein said securing means secures said plate and said absorbent material proximate to the stoma such that said plate is spaced in the range of about two to three inches away from the stoma.

14. The shield according to claim 1 wherein said plate is also adapted to facilitate a person's hands being interposed between the torso skin immediately surrounding the stoma and said plate such that the person's hands may manipulate the at least a portion of the ostomy pouching system and wherein said securing means secures said plate and said absorbent material proximate to the stoma such that said plate facilitates a person's hands being interposed between the torso skin immediately surrounding the stoma and said plate such that the person's hands may manipulate the at least a portion of the ostomy pouching system.

15. A shield adapted for use in connection with changing portions of an ostomy pouching system in association with a stoma through which body waste flows, said shield comprising:
 a plate adapted to be disposed over the stoma and at least a portion of the ostomy pouching system;
 an absorbent material adapted to absorb body waste flowing from the stoma, said absorbent material disposed adjacent to a portion of said plate and fashioned in a pocket configuration; and
 means for selectively securing said plate and said absorbent material proximate to the stoma such that said plate is disposed over the stoma and at least a portion of the ostomy pouching system and such that said absorbent material is disposed beneath the stoma and at least a portion of the ostomy pouching system.

16. The shield according to claim 15 wherein said securing means includes an adhesive layer covered by a sheet adapted to be peeled away from said adhesive layer in order to expose said adhesive layer such that said adhesive layer can be applied against the body proximate to the stoma.

17. The shield according to claim 15 wherein said plate is fashioned in a substantially planar configuration and is manually bendable into a substantially cupped configuration.

18. The shield according to claim 15 wherein said plate is preformed into a substantially cupped, arcuate, bowed configuration.

19. The shield according to claim 15 wherein said absorbent material possesses a substantially pocket configuration extending along and maintained against the peripheral edge of said plate, with the mouth portion of the pocket facing away from the plate peripheral edge and wherein said securing means includes a strip of adhesive extending along and maintained against said absorbent material.

20. The shield according to claim 15 wherein a surface of said plate possesses an area substantially in the range of about twenty to one hundred forty square inches, which surface is adapted to face the stoma and at least a portion of the ostomy pouching system.

21. A shield adapted for use in connection with changing portions of an ostomy pouching system in association with a stoma through which body waste flows, said shield comprising:
 a plate adapted to be disposed over and spaced away from the stoma and at least a portion of the ostomy pouching system and adapted to facilitate a person's hands being interposed between the stoma and said plate such that a person's hands may manipulate the at least a portion of the ostomy pouching system;
 an absorbent material adapted to absorb body waste flowing from the stoma, said absorbent material disposed adjacent to a portion of said plate; and
 means for selectively securing said plate and said absorbent material proximate to the stoma such that said plate is disposed over and spaced away from the stoma and at least a portion of the ostomy pouching system, such that said absorbent material is disposed beneath the stoma and at least a portion of the ostomy pouching system, and such that said plate facilitates a person's hands being interposed between the stoma and said plate such that a person's hands may manipulate the at least a portion of the ostomy pouching system.

22. The shield according to claim 21 wherein said securing means includes an adhesive layer covered by a sheet adapted to be peeled away from said adhesive layer in order to expose said adhesive layer such that said adhesive layer can be applied against the body proximate to the stoma.

23. The shield according to claim 21 wherein said plate is fashioned in a substantially planar configuration and is manually bendable into a substantially cupped configuration.

24. The shield according to claim 21 wherein said plate is preformed into a substantially cupped, arcuate, bowed configuration.

25. A shield according to claim 21 wherein said absorbent material is fashioned in a pocket configuration.

26. The shield according to claim 21 wherein said absorbent material possesses a substantially pocket configuration extending along and maintained against the peripheral edge of said plate, with the mouth portion of the pocket facing away from the plate peripheral edge and wherein said securing means includes a strip of adhesive extending along and maintained against said absorbent material.

27. The shield according to claim 21 wherein a surface of said plate possesses an area substantially in the range of about twenty to one hundred forty square inches, which surface is adapted to face the stoma and at least a portion of the ostomy pouching system.

* * * * *